US012502533B2

(12) United States Patent
Chalavoutis

(10) Patent No.: US 12,502,533 B2
(45) Date of Patent: Dec. 23, 2025

(54) ADHESIVE HOUSING FOR CARDIAC DEVICE INHIBITOR

(71) Applicant: PGX Platinum Health LLC, Carle Place, NY (US)

(72) Inventor: Michael Chalavoutis, Melville, NY (US)

(73) Assignee: PGX Platinum Health LLC, Carle Place, NY (US)

( * ) Notice: Subject to any disclaimer, the term of this patent is extended or adjusted under 35 U.S.C. 154(b) by 285 days.

(21) Appl. No.: 18/477,682

(22) Filed: Sep. 29, 2023

(65) Prior Publication Data

US 2025/0108209 A1 Apr. 3, 2025

(51) Int. Cl.
*A61N 1/08* (2006.01)
*A61N 1/39* (2006.01)

(52) U.S. Cl.
CPC ............. *A61N 1/08* (2013.01); *A61N 1/3956* (2013.01)

(58) Field of Classification Search
CPC ................................ A61N 1/08; A61N 1/3956
See application file for complete search history.

(56) References Cited

U.S. PATENT DOCUMENTS

| | | | |
|---|---|---|---|
| 7,489,495 B2 | 2/2009 | Stevenson | |
| 8,386,051 B2 | 2/2013 | Rys | |
| 8,639,335 B2 | 1/2014 | Peichel et al. | |
| 8,954,030 B1 | 2/2015 | Buchheit | |
| 9,008,799 B2 | 4/2015 | Stevenson et al. | |
| 10,589,023 B2 | 3/2020 | Cindrich et al. | |
| 11,633,610 B2 | 4/2023 | Chin et al. | |
| 2012/0283588 A1* | 11/2012 | Lowy | A61N 1/37217 600/511 |
| 2019/0009097 A1 | 1/2019 | Hartley et al. | |
| 2022/0062623 A1* | 3/2022 | Takabu | C09J 201/00 |

FOREIGN PATENT DOCUMENTS

WO 2020213775 A1 10/2020

* cited by examiner

*Primary Examiner* — Ankit D Tejani
*Assistant Examiner* — Joshua Brendon Solomon
(74) *Attorney, Agent, or Firm* — Dilworth & Barrese, LLP.

(57) ABSTRACT

An adhesive housing is adapted to hold a magnet. The adhesive housing is placed on a person so that the functionality of an implanted cardiac device is affected. The adhesive housing and magnet inhibits the functions of an implanted cardiac device so that, for example, inappropriate shocks do not occur.

20 Claims, 5 Drawing Sheets

ADHESIVE HOUSING FOR CARDIAC DEVICE INHIBITOR

FIELD OF INVENTION

The present teachings relate to EMI inhibitors for cardiac devices, and to providing an adhesive magnet housing to attach to a person to prevent a cardiac device from accidentally harming a patient.

BACKGROUND

During surgical procedures electromagnetic interference (EMI) can interfere with the operation of cardiac devices, such as an implantable cardi-defibrillator (ICD) or pacemaker. To prevent the cardiac devices from incorrectly detecting arrythmia and incorrectly shocking the patient, magnets are placed on the devices. These convert cardiac devices into an asynchronous mode and prevent oversensing by the cardiac devices.

During a surgical procedure a magnet is placed over the area on a patient where the cardiac device would be located. This magnet is held in place using tape. This method of taping the magnet to the chest is inadequate with respect to making certain that the magnet is properly held in place in a consistent manner.

There remains a need to ensure that when a magnet is used it is properly placed on the patient and sufficiently held in place.

SUMMARY

An aspect of the disclosure is a system and method for disabling a cardiac device using an adhesive housing.

An aspect of the disclosure is an adhesive magnet housing for use with cardiac devices. The adhesive magnet housing comprises a first layer comprising adhesive material; a second layer comprising at least two liner portions, wherein removal of one of the at least two liner portions exposes a first portion of the adhesive material located on the first layer, wherein the first portion of the adhesive material is adapted to adhesively retain a magnet, wherein removal of another one of the at least two liner portions exposes a second portion of the adhesive material located on the first layer; and wherein the one of the at least two liner portions is substantially surrounded by another one of the at least two liner portions.

Another aspect of the disclosure is an adhesive magnet housing for use with cardiac devices. The adhesive magnet housing comprising a first layer comprising adhesive material; a second layer comprising a first liner portion and a second liner portion; a magnet located between the first layer and the first liner portion, wherein removal of the first liner portion exposes the magnet, wherein removal of the second liner portion exposes a second portion of the adhesive material; and wherein the first liner portion is substantially surrounded by the second liner portion.

Still yet another aspect of the invention is a method of attaching a magnet to a person's chest. The method comprising removing a first liner portion from a first layer comprising adhesive material, wherein the first liner portion is substantially surrounded by a second liner portion, placing a magnet between the first layer and the first liner portion, wherein the magnet is adhesively attached to the first layer, removing the second liner portion and exposing a second portion of the adhesive material; and adhesively attaching the second liner portion to the person's chest.

The foregoing as well as other features and advantages of the present teachings will be more fully understood from the following figures, description, detailed exemplary embodiments, and claims.

BRIEF DESCRIPTION OF THE DRAWINGS

The drawings described herein are for illustration purposes only. The drawings are not necessarily to scale, with emphasis generally being placed upon illustrating the principles of the present teachings. The drawings are not intended to limit the scope of the present teachings in any way. Like numerals generally refer to like parts.

DETAILED DESCRIPTION

Figure 1:
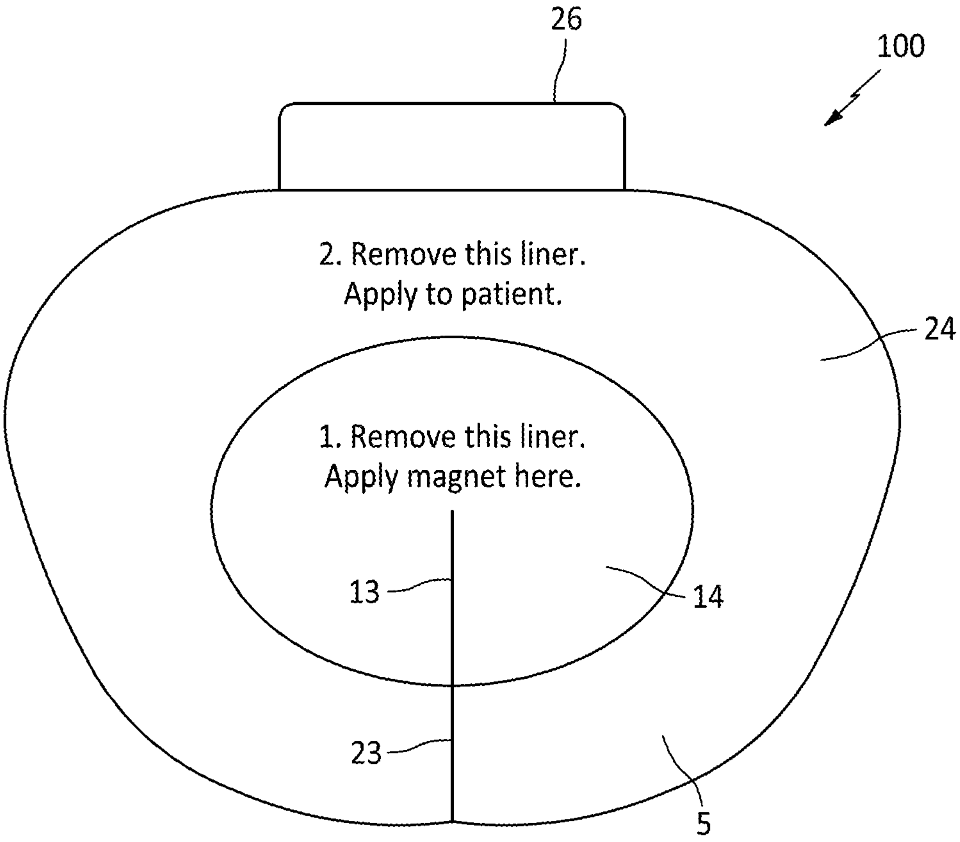
FIG. 1 is a top-down view of the adhesive magnet housing.

It is to be understood that the invention herein is not limited to the particular procedures, materials and modifications described herein and as such may vary. It is also to be understood that the terminology used is for purposes of describing particular embodiments only and is not intended to limit the scope of the present invention which will be limited only by the appended claims.

In the specification and claims herein, the following terms and expressions are to be understood as indicated.

The singular forms "a," "an," and "the" include the plural.

All methods described herein may be performed in any suitable order unless otherwise indicated herein or otherwise clearly contradicted by context. The use of any and all examples, or exemplary language provided herein, e.g., "such as", is intended merely to better illuminate the invention and does not pose a limitation on the scope of the invention unless otherwise claimed. No language in the specification should be construed as indicating any non-claimed element as essential to the practice of the invention.

As used herein, "comprising," including," "containing," "characterized by", and grammatical equivalents thereof are inclusive or open-ended terms that do not exclude additional, unrecited elements or method steps, but will also be understood to include the more restrictive terms "consisting of" and "consisting essentially of."

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints of such ranges or sub-ranges.

It will be further understood that any compound, material, or substance which is expressly or implicitly disclosed in the specification and/or recited in a claim as belonging to a group of structurally, compositionally and/or functionally related compounds, materials or substances includes individual representatives of the group and all combinations thereof.

A cardiac device, such as a pacemaker or implantable cardiac-defibrillator (ICD), may be subjected to electromagnetic interference (EMI) during a surgical procedure. A magnet may be used to place the cardiac device into asynchronous mode in some cardiac devices.

The types of magnets used to place cardiac devices into asynchronous modes are specifically designed for medical purposes and are typically referred to as "programming magnets" or "pacemaker/ICD magnets." These magnets are used by qualified medical professionals to interact with the cardiac device's programming system and make necessary adjustments to its operating mode.

Programming magnets are engineered to create a specific magnetic field that can communicate with the device's internal programming circuitry. When placed over the patient's skin, in the area where the cardiac device is implanted, the magnet can trigger the device to switch into asynchronous mode or perform other programming changes as needed.

In the context of a cardiac device, asynchronous mode refers to a specific operating mode where the cardiac device's pacing or shocking functions are decoupled from the patient's own cardiac electrical activity. In this mode, the cardiac device generates electrical impulses regardless of the heart's natural rhythm, providing a fixed rate of pacing or shocking.

Being able to provide an easy method for applying a magnet to a patient in a secure manner is preferable than past methods. Described herein is a method and device that is adapted to secure a magnet to a patient to place the cardiac device into asynchronous mode and/or otherwise prevent a cardiac device from causing harm during a surgical procedure.

Referring to FIG. 1, shown is a top-down view of the adhesive magnet housing 100. The adhesive magnet housing 100 is adapted to secure a magnet into position on a person's chest.

Shown in FIG. 1 is the liner layer 5. Liner layer 5 is made of a non-stick material that permits removal of the liner layer 5 from the adhesive material. The liner layer material may be a type of non-stick polymer. This material may be a low-adherent or non-adherent film. A material used for this purpose may be polyethylene or a combination of polyethylene and other polymers. These materials have non-stick properties while still allowing air and moisture to pass through, aiding in the healing process. In an embodiment, the liner is poly-coated Kraft paper, silicone release on one side and having a thickness of about 0.15 mm. This type of liner may be found used in 3M™ Single Coated Medical White Nonwoven Tape on Liner, Product 1776.

Liner layer 5 comprises a first liner portion 14 that is oval in shape. In an embodiment, the first liner portion is rectangular in shape. In an embodiment, the first liner portion is pentagonal in shape. In an embodiment, the first liner portion is hexagonal in shape. In an embodiment, the first liner portion is octagonal in shape. In an embodiment, the first liner portion is circular in shape. In an embodiment, the first liner portion is triangular in shape. In an embodiment, the first liner portion is irregular in shape. In an embodiment, the first liner portion is shaped to correspond to the shape of the magnet that is being implemented in the surgery.

In the embodiment shown in FIG. 1 the first liner portion 14 is oval in shape. The oval shaped first liner portion 14 is sized to cover adhesive material located below it that is adapted to secure a magnet to a person's chest. The first liner portion 14 is shaped to cover the magnet that is implemented to place the cardiac device in asynchronous mode.

The first liner portion 14 has slit 13 formed in a portion of it. The slit 13 is formed to facilitate the removal of the first liner portion 14 prior to placement of a magnet.

The first liner portion 14 is separated from second liner portion 24 so that each portion can be removed separately. The second liner portion 24 substantially surrounds the first liner portion 14. The second liner portion 24 is adjacent to the perimeter of the first liner portion 14. Extending from the second liner portion 24 along its perimeter is a third liner portion 26.

If the third liner portion 26 is considered to be the top of the liner layer 5 when viewing the adhesive magnet housing top-down. The second liner portion 24 is shaped so that it is wider in the area below the third liner portion 26 and above the mid-line of the first liner portion 15. The width of the second liner portion 24 narrows as it extends downward. The second liner portion 24 has a general shape like an apple or heart. The size and shape of the second liner portion 24 is adapted to cover the adhesive portion.

The second liner portion 24 may either completely or incompletely surround the perimeter of the first liner portion 14. In an embodiment, the second liner portion is circular in shape. In an embodiment, the second liner portion is rectangular in shape. In an embodiment, the second liner portion is pentagonal in shape. In an embodiment, the second liner portion is hexagonal in shape. In an embodiment, the second liner portion is octagonal in shape. In an embodiment, the second liner portion is oval in shape. In an embodiment, the second liner portion is triangular in shape. In an embodiment, the second liner portion is irregular in shape. In an embodiment, the second liner portion is shaped to correspond to the shape of the magnet that is being implemented in the surgery.

The second liner portion 24 has slit 23 formed in a portion of it. The slit 23 is formed in order to facilitate the removal of the second liner portion 24 prior to placement of the magnet on a person.

In an embodiment, the second liner portion 24 is about 136.91 mm in width at its widest. In an embodiment, the second liner portion 24 is between 135 and 155 mm in width at its widest. In an embodiment, the second liner portion 24 is between 130 and 160 mm in width at its widest. In an embodiment, the distance between the top of the second liner portion 24 and the bottom of the second liner portion 24 is about 133.48 mm in length. In an embodiment, the distance between the top of the second liner portion 24 and the bottom of the second liner portion 24 is between 130 and 140 mm in length. In an embodiment, the distance between the top of the second liner portion 24 and the bottom of the second liner portion 24 is between 125 and 145 mm in length.

The third liner portion 26 is rectangular in shape. The rectangular shape helps a user manipulate the adhesive magnet housing 100 when securing a magnet to a person so that the adhesive material that surrounds and helps secure the magnet does not have to be interfered with.

In an embodiment, the third liner portion 26 is about 51.08 mm in width. In an embodiment, the third liner portion 26 is between 45 and 55 mm in width. In an embodiment, the third liner portion 26 is between 40 and 60 mm in width. In an embodiment, the distance between the top of the third liner portion 26 and the bottom of the second liner portion 24 is about 152.53 mm in length. In an embodiment, the distance between the top of the third liner portion 26 and the bottom of the second liner portion 24 is between 145 and 155 mm in length. In an embodiment, the distance between the top of the third liner portion 26 and the bottom of the second liner portion 24 is between 140 and 160 mm in length.

In an embodiment, the third liner portion is circular in shape. In an embodiment, the third liner portion is rectangular in shape. In an embodiment, the third liner portion is pentagonal in shape. In an embodiment, the third liner portion is hexagonal in shape. In an embodiment, the third liner portion is octagonal in shape. In an embodiment, the third liner portion is oval in shape. In an embodiment, the third liner portion is triangular in shape. In an embodiment, the third liner portion is irregular in shape.

Figure 2:
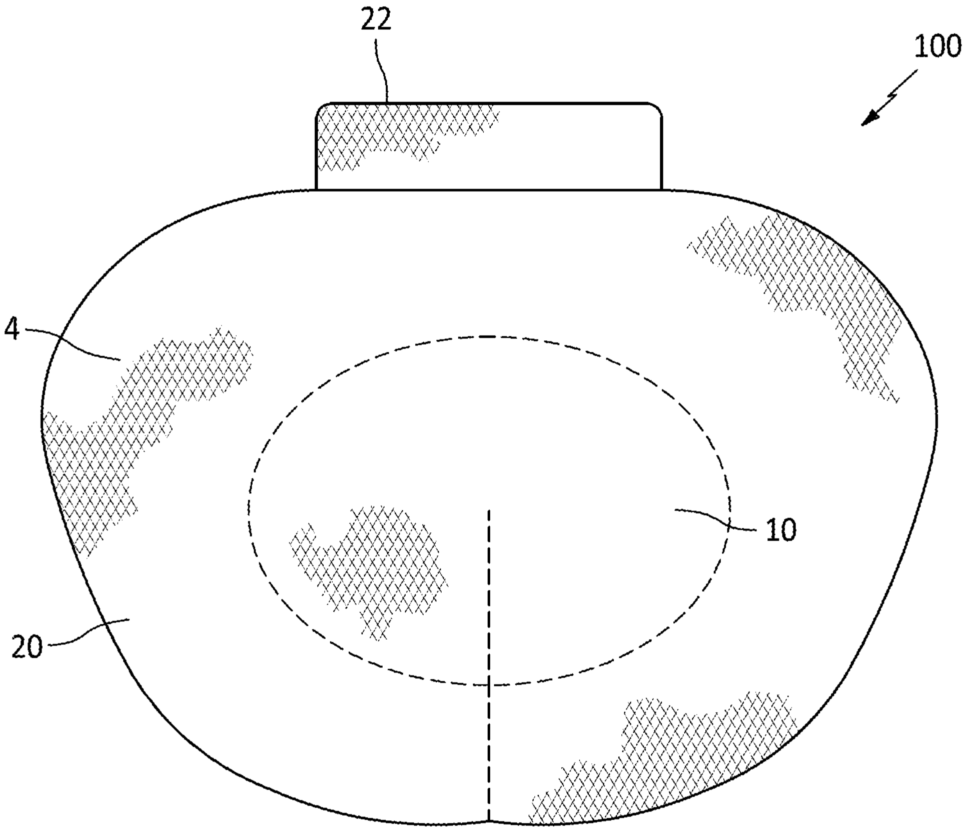
FIG. 2 is a top-down view of the adhesive magnet housing showing the liner portions removed and the adhesive sections exposed.

FIG. 2 is a top-down view of the adhesive magnet housing 100 showing the liner portions removed and the adhesive sections exposed. Shown in FIG. 1 is the adhesive layer 4. The adhesive layer 4 is made of made of an adhesive material and backing that permits adhesively securing a magnet and adhesively attaching the adhesive magnet housing 100 to a person. The adhesive layer material may be made from medical-grade adhesive materials. Adhesives may be acrylic-based or rubber-based adhesives. These adhesives provide a gentle yet secure bond to the skin without causing irritation. The adhesive material may be non-tackified acrylic-based adhesive on 100% polyester white spunlace nonwoven, printable material that is roughly 0.3 mm in thickness. This type of adhesive and backing may be found used in 3M™ Single Coated Medical White Nonwoven Tape on Liner, Product 1776. In an embodiment, the adhesive material is 10 mils (~0.3 mm) of white spunlace polyester nonwoven tape, with 100% polyester white spunlace nonwoven, printable fabric. The adhesive is a non-tackified acrylic-based adhesive developed for medical use. The backing liner comprises of 83 lb. Poly-coated kraft paper, silicone release on one side, 6 mils+/−0.6 mils (0.15 mm+/−0.015 mm).

Medical-grade adhesives are specially formulated adhesives designed and manufactured to meet the requirements of medical applications. These adhesives are used in various medical devices, wound dressings, and skin-adhered products. They should adhere securely to the skin or other medical substrates while preferably being gentle and non-irritating.

Medical-grade adhesives are preferably biocompatible, meaning they do not cause adverse reactions when they come into contact with living tissue. Medical-grade adhesives preferably are able to withstand common sterilization methods such as gamma radiation, ethylene oxide gas, or electron beam irradiation. This ensures that the adhesive remains safe and effective after the sterilization process. Medical-grade adhesives are preferably used in wound dressings or other skin-adhered products should allow the skin to breathe, preventing moisture buildup and reducing the risk of skin maceration. Medical-grade adhesives preferably are able to provide a secure bond to the skin or other substrates over an extended period without prematurely detaching or causing skin trauma upon removal. Medical adhesives preferably do not contain harmful substances that could leach into the body or cause toxicity.

The adhesive layer 4 comprises a first adhesive portion 10 that is oval in shape and corresponds to the shape of the first liner portion 14. In an embodiment, the first adhesive portion is rectangular in shape. In an embodiment, the first adhesive portion is pentagonal in shape. In an embodiment, the first adhesive portion is hexagonal in shape. In an embodiment, the first adhesive portion is octagonal in shape. In an embodiment, the first adhesive portion is circular in shape. In an embodiment, the first adhesive portion is triangular in shape. In an embodiment, the first adhesive portion is irregular in shape. In an embodiment, the first adhesive portion is shaped to correspond to the shape of the magnet that is being implemented in the surgery.

In the embodiment shown in FIG. 2 the first adhesive portion 10 is oval in shape. The oval shaped first adhesive portion 10 is adapted to secure a magnet to a person's chest. The first adhesive portion 10 is shaped to cover the magnet that is implemented to place the cardiac device in asynchronous mode.

The first adhesive portion 10 is separated from second adhesive portion 20 so that when a magnet is placed on the first adhesive portion 10, the second adhesive portion 20 substantially surrounds the first adhesive portion 10. The second adhesive portion 20 is adjacent to the perimeter of the first adhesive portion 10. Extending from the second adhesive portion 20 along its perimeter is a third adhesive portion 22. In an embodiment the second adhesive portion is made from the same adhesive material as the first adhesive portion. In an embodiment the second adhesive portion is made from a different adhesive material than the first adhesive portion.

If the third adhesive portion 22 is considered to be the top of the adhesive layer 4 when viewing the adhesive magnet housing 100 top-down. The second adhesive portion 20 is shaped so that it is wider in the area below the third adhesive portion 22 and above the mid-line of the first adhesive portion 10. The width of the second adhesive portion 20 narrows as it extends downward. The second adhesive portion 20 has a general shape like an apple or heart. The size and shape of the second adhesive portion 20 is adapted to be commensurate with the liner portion.

The second adhesive portion 20 may either completely or incompletely surround the perimeter of the first liner portion 14. In an embodiment, the second adhesive portion is circular in shape. In an embodiment, the second adhesive portion is rectangular in shape. In an embodiment, the second adhesive portion is pentagonal in shape. In an embodiment, the second adhesive portion is hexagonal in shape. In an embodiment, the second adhesive portion is octagonal in shape. In an embodiment, the second adhesive portion is oval in shape. In an embodiment, the second adhesive portion is triangular in shape. In an embodiment, the second adhesive portion is irregular in shape. In an embodiment, the second adhesive portion is shaped to correspond to the liner.

The third adhesive portion 22 is rectangular in shape. The rectangular shape helps a user manipulate the adhesive magnet housing 100 when securing a magnet to a person so that the adhesive material that surrounds and helps secure the magnet does not have to be interfered with. The third adhesive portion 22 additionally provides an area for a user of the adhesive magnet housing 100 to grab to remove the adhesive magnet housing 100 from the person.

In an embodiment, the third adhesive portion is circular in shape. In an embodiment, the third liner portion is rectangular in shape. In an embodiment, the third adhesive portion is pentagonal in shape. In an embodiment, the third adhesive portion is hexagonal in shape. In an embodiment, the third adhesive portion is octagonal in shape. In an embodiment, the third adhesive portion is oval in shape. In an embodiment, the third adhesive portion is triangular in shape. In an embodiment, the third adhesive portion is irregular in shape. In an embodiment, the third adhesive portion is shaped to correspond to liner.

Figure 3:
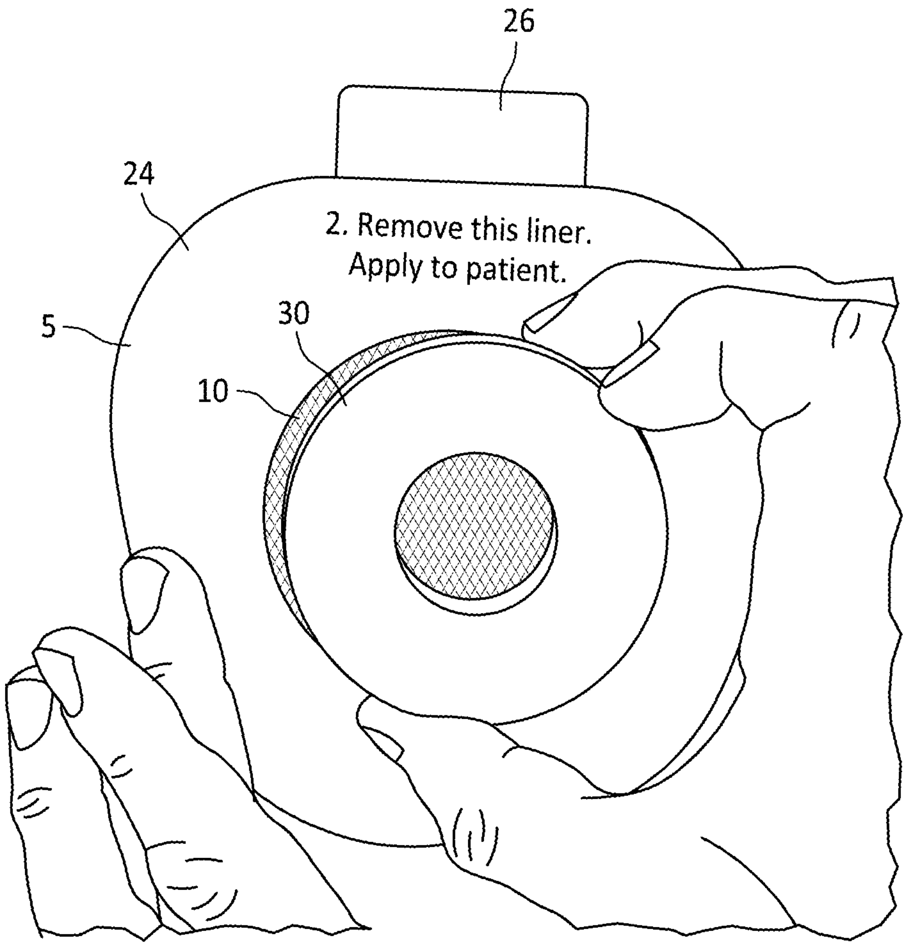
FIG. 3 is a view of the placement of a magnet on the adhesive portion of the adhesive magnet housing.

FIG. 3 is a view of magnet 30 being placed on first adhesive portion 10. In FIG. 3 the first liner portion 14 has been removed and the first adhesive portion 10 has been exposed. The magnet 30 is then placed on the first adhesive portion 10. After being placed on the first adhesive portion 30, the second liner portion 24 and the third liner portion 26 will be removed prior to placement of the magnet 30 on a person. Third liner portion 26 assists in the removal of the liner portions. The sides of magnet 30 may be secured by the adhesive portions after placement on the person to ensure stability.

The strength of the magnet 30 is carefully calibrated to produce the desired effect on a cardiac device's programming. It needs to be strong enough to penetrate the skin and interact with the device but not so strong that it causes any damage to the device or surrounding tissues.

In an embodiment the strength of the magnet 30 is greater than 10 Gauss. In an embodiment the strength of the magnet 30 is less than 90 Gauss. In an embodiment, the strength of the magnet 30 is between 30 and 40 Gauss. In an embodiment, the strength of the magnet 30 is between 30 and 50 Gauss. In an embodiment, the strength of the magnet 30 is between 30 and 60 Gauss. In an embodiment, the strength of the magnet 30 is between 30 and 70 Gauss. In an embodiment, the strength of the magnet 30 is between 30 and 80 Gauss.

Pacemaker/ICD magnets are usually small and flat, with a specific shape that allows for placement over a person's heart. The size and shape of the magnet 30 ensures accurate targeting of the device's programming circuitry. The magnetic field of the programming magnet is designed to interact with the specific sensor or receptor within the cardiac device responsible for programming changes. The orientation of the magnetic field is used for proper communication. The materials used in the construction of these magnets may be biocompatible. In an embodiment, the magnet is a grade N52 super strong neodymium magnet ring OD 1.26"×ID ½"×⅜".

Figure 4:
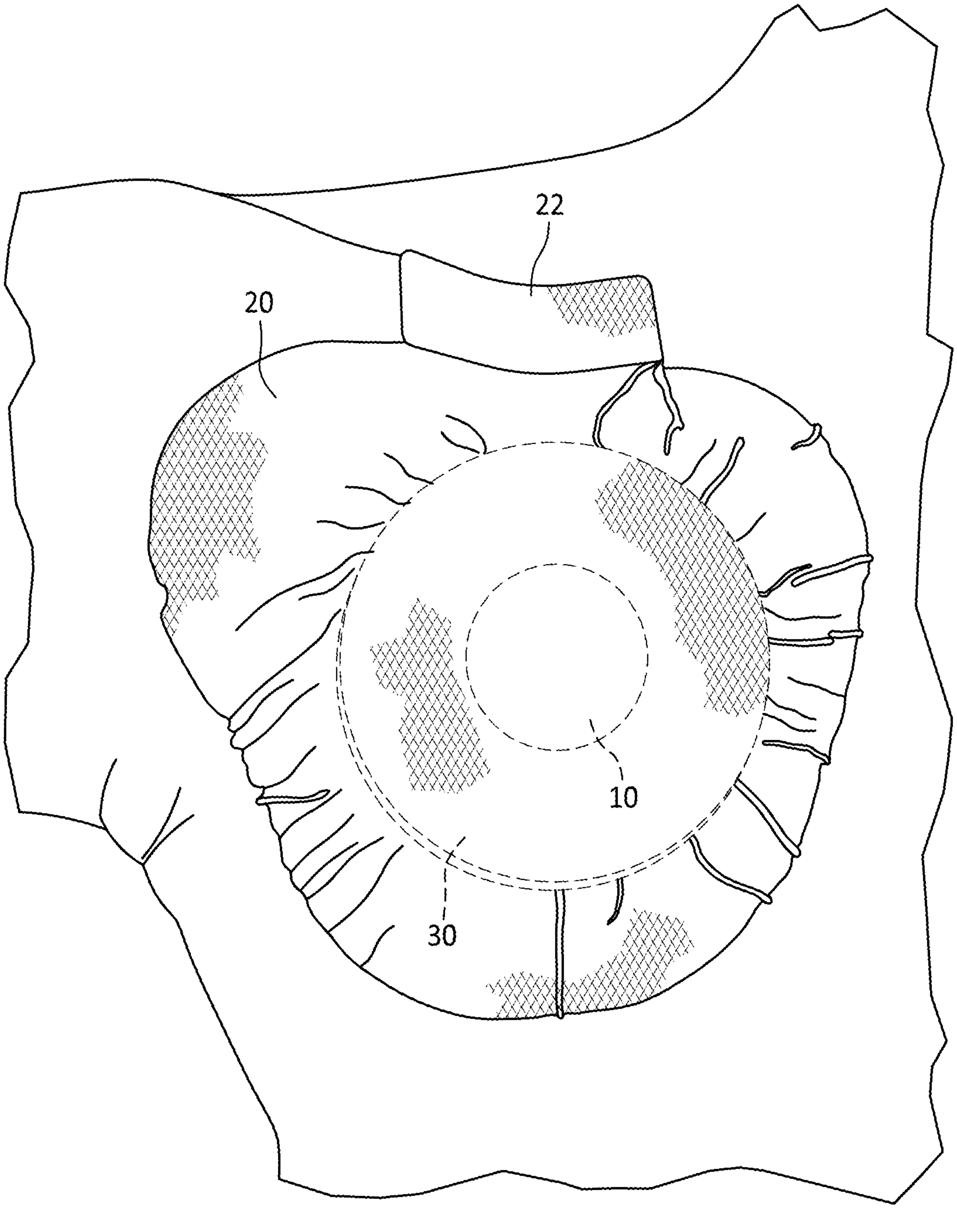
FIG. 4 is a view of the adhesive magnet housing attached to a person.

FIG. 4 shows the magnet 30 secured to the chest of a person. The second adhesive portion 20 is large enough so that it adequately secures the magnet 30 to the chest of a person. The shape of the second adhesive portion 20 is so that it can conform to the chest of a person. In FIG. 4, the third adhesive 22 portion is uncovered. In FIG. 3, the third liner portion 26 remains attached and is used for removal and attachment of the adhesive magnet housing 100.

Figure 5:
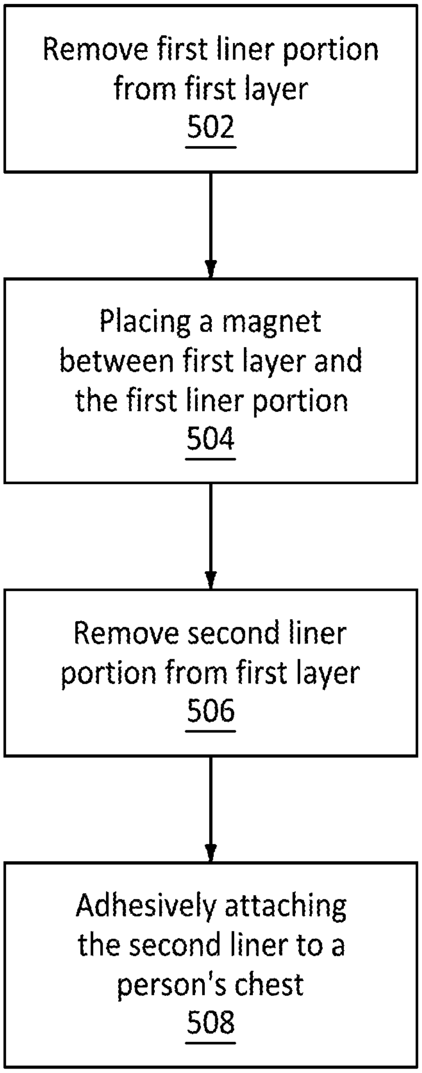
FIG. 5 is a flow chart setting forth the method for placing the magnet on a person.

FIG. 5 is a flow chart setting forth the method for placing the magnet 30 on a person. In step 502 the first liner portion 14 is removed from the adhesive layer 4. In step 504, the magnet 30 is placed on the first adhesive portion 10. In step 506 the second liner portion 24 is removed from the adhesive layer 4. In step 508 the magnet and the second liner are adhesively attached to a person's chest. By doing this the implanted cardiac device is prevented from inadvertently harming a person.

In an embodiment, the adhesive magnet housing 100 is packaged with the magnet 30 already attached to the adhesive layer 4. This allows there to be an entire packaged solution for rendering cardiac devices harmless for patients. In this embodiment, the adhesive magnet housing 100 contains a magnet 30 that is appropriate for a predetermined cardiac device. Adhesive magnet housing 100 can be prepackaged for different types of cardiac devices. Additionally, the adhesive magnet housing 100 is shaped in a manner that is distinguishable from other adhesive devices. This allows hospital staff to appropriately identify the device, and not mistake it for another medical device patch (external defibrillator pad/pressure dressing).

All referenced publications, if any, are incorporated by reference herein in their entirety for the purpose of describing and disclosing, for example, materials, constructs, and methodologies that can be used in connection with the presently described invention.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

The invention claimed is:

1. An adhesive magnet housing for use with cardiac devices comprising:

a first layer comprising adhesive material;

a second layer comprising at least two liner portions, wherein removal of one of the at least two liner portions exposes a first portion of the adhesive material located on the first layer, wherein the first portion of the adhesive material is adapted to adhesively retain a magnet, wherein removal of another one of the at least two liner portions exposes a second portion of the adhesive material located on the first layer; and wherein the one of the at least two liner portions is substantially surrounded by another one of the at least two liner portions.

2. The adhesive magnet housing of claim 1, wherein the another one of the at least two liner portions has a width greater than the one of the at least two liner portions.

3. The adhesive magnet housing of claim 1, wherein the one of the at least two liner portions is circular shaped.

4. The adhesive magnet housing of claim 1, wherein the another one of the at least two liner portions has a variable width.

5. The adhesive magnet housing of claim 1, wherein the first portion of the adhesive material comprises a different composition of adhesive material than the second portion of the adhesive material.

6. The adhesive magnet housing of claim 1, wherein the second portion of the adhesive material is adapted to adhesively attach to a person.

7. The adhesive magnet housing of claim 1, further comprising a third liner portion that is rectangular in shape and extends from the other of the at least two liner portions.

8. An adhesive magnet housing for use with cardiac devices comprising:

a first layer comprising adhesive material;

a second layer comprising a first liner portion and a second liner portion;

a magnet located between the first layer and the first liner portion, wherein removal of the first liner portion exposes the magnet, wherein removal of the second liner portion exposes a second portion of the adhesive material; and wherein the first liner portion is substantially surrounded by the second liner portion.

9. The adhesive magnet housing of claim 8, wherein the second liner portion has a width greater than the first liner portion.

10. The adhesive magnet housing of claim 8, wherein the first liner portion is circular shaped.

11. The adhesive magnet housing of claim 8, wherein the second liner portion has a variable width.

12. The adhesive magnet housing of claim 8, wherein the first portion of the adhesive material comprises a different composition of adhesive material than the second portion of the adhesive material.

13. The adhesive magnet housing of claim 8, wherein the second portion of the adhesive material is adapted to adhesively attach to a person.

14. The adhesive housing of claim 1, wherein the liner layer has a third liner portion that is an extension that is rectangular in shape.

15. A method of attaching a magnet to a person's chest, the method comprising:

removing a first liner portion from a first layer comprising adhesive material, wherein the first liner portion is substantially surrounded by a second liner portion, placing a magnet between the first layer and the first liner portion, wherein the magnet is adhesively attached to the first layer, removing the second liner portion and exposing a second portion of the adhesive material; and adhesively attaching the second liner portion to the person's chest.

16. The method of claim 15, wherein the second liner portion has a width greater than the first liner portion.

17. The method of claim 15, wherein the first liner portion is circular shaped.

18. The method of claim 15, wherein the second liner portion has a variable width.

19. The method of claim 15, wherein the first portion of the adhesive material comprises a different composition of adhesive material than the second portion of the adhesive material.

20. The method of claim 15, wherein the liner layer has a third liner portion that is an extension that is rectangular in shape.

* * * * *